United States Patent [19]

Vipond et al.

[11] Patent Number: 5,616,811
[45] Date of Patent: Apr. 1, 1997

[54] ETHERAMINE ALKOXYLATES

[75] Inventors: Jeffrey J. Vipond; John M. Larkin; Terry L. Renken, all of Austin; Howard M. Stridde, Georgetown, all of Tex.

[73] Assignee: Huntsman Petrochemical Corporation, Salt Lake City, Utah

[21] Appl. No.: 470,692

[22] Filed: Jun. 6, 1995

[51] Int. Cl.$^6$ ................................. C07C 211/03
[52] U.S. Cl. .................. 564/505; 564/399; 564/424; 564/475; 564/504
[58] Field of Search ...................... 564/504, 505, 564/506, 399, 474, 475

[56] References Cited

U.S. PATENT DOCUMENTS

| | | | |
|---|---|---|---|
| 2,290,880 | 7/1942 | Katzman | 260/584 |
| 4,014,806 | 3/1977 | Connor et al. | 252/110 |
| 4,395,373 | 7/1983 | Login et al. | 260/928 |
| 4,405,356 | 9/1983 | Sikorski et al. | 71/87 |
| 4,407,764 | 10/1983 | Sikorski et al. | 260/940 |
| 4,465,802 | 8/1984 | Dennen et al. | 524/395 |
| 4,666,620 | 5/1987 | Foresberg | 252/75 |
| 4,908,150 | 3/1990 | Hessel et al. | 252/174.12 |
| 5,082,585 | 1/1992 | Hessel et al. | 252/174.12 |
| 5,159,101 | 10/1992 | Champion et al. | 558/450 |
| 5,314,747 | 5/1994 | Malhotra et al. | 428/341 |
| 5,352,835 | 10/1994 | Dai et al. | 564/480 |

FOREIGN PATENT DOCUMENTS 0290416A 11/1988 European Pat. Off. .
1588079 4/1981 United Kingdom .

*Primary Examiner*—Brian M. Burn
*Attorney, Agent, or Firm*—Russell R. Stolle; Ron D. Brown; David L. Mossman

[57] ABSTRACT

Etheramine alkoxylates are described which have the formula:

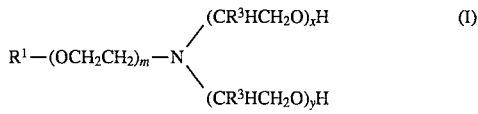

where $R^1$ is a straight or branched alkyl, aryl or alkylaryl group of 6 to 22 carbon atoms; $R^3$ are independently hydrogen or $C_1$ to $C_3$ alkyl; m averages from about 1 to about 20; and x and y each independently average from about 0 to 30, where x+y averages from about 2 to about 60. These etheramine alkoxylates have surfactant properties. Further, they may be quaternized to make other compounds which will have useful surfactant properties.

8 Claims, No Drawings

ETHERAMINE ALKOXYLATES

FIELD OF THE INVENTION

The invention relates to etheramine alkoxylates, and more particularly relates, in one aspect of the invention, to etheramine alkoxylates and methods of preparation therefor which involve aminating aryl polyalkoxylates and alkyl polyalkoxylates.

BACKGROUND OF THE INVENTION

Ethoxylated tallowamines and other compounds have various uses, such as surfactants and emulsifiers. However, the tallowamine raw material can be expensive. In addition, ethoxylated alkylamine surfactants of the prior art is that when included in concentrate formulation, they tend to be an irritant to the eyes.

A further drawback of ethoxylated alkylamine surfactants of the prior art is that when water is added to them, they tend to form a stiff gel which adds to the complexity and expense of manufacturing formulations containing such surfactants, by making it difficult to clean vessels and pipes. In practice, this problem is alleviated by adding an anti-gelling agent, such as polyethylene glycol to the surfactant.

European Patent No. 0 290 416 to Forbes, et al. discloses compositions of glyphosate salts comprising ethoxylated alkylamine surfactants having less than 15 moles of EO. For example, a composition is disclosed comprising the isopropylamine salt of glyphosate and an ethoxylated cocoamine surfactant having an average of 5 moles of EO. It is taught by this patent that certain herbicidal efficacy advantages are obtainable with such compositions by comparison with compositions where the EO level in the surfactant is around 15 moles.

United Kingdom Patent No. 1,588,079 to Texaco Development Corporation discloses examples of such surfactants and methods for preparing them, and suggests that they are useful as detergents, dispersants, wetting agents and emulsifiers. Surfactants disclosed have the formula:

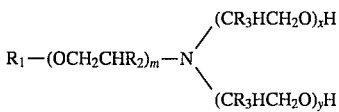

where $R_1$ is a $C_8$–$C_{18}$ alkyl; $R_2$ is methyl; $R_3$ is hydrogen; m is a number from 1 to 5; and x and y are average numbers such that x+y is in the range from 2 to 20.

It would be desirable if surfactant compounds with similar functionalities to the ethoxylated alkylamines used in the prior art, but without some of their attendant disadvantages could be discovered.

SUMMARY OF THE INVENTION

Accordingly, it is an object of the present invention to provide etheramine alkoxylates made without using tallowamine.

It is another object of the present invention to provide etheramine alkoxylates having potential for use as wetting agents, surfactants, emulsifiers and detergents.

Another object of the invention is to provide etheramine alkoxylates having less steric bulk than tallowamine alkoxylates and thus being easier to quaternize to make potential surfactants.

In carrying out these and other objects of the invention, there is provided, in one form, etheramine alkoxylates of the formula:

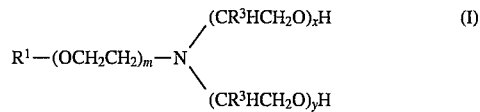

where $R^1$ is a straight or branched alkyl, aryl or alkylaryl group of 6 to 22 carbon atoms; $R^3$ are independently hydrogen or $C_1$–$C_3$ alkyl; m averages from about 1 to about 20; and x and y each independently average from about 0 to 30, where x+y averages from about 2 to about 60 and where x and y are not both 0.

DETAILED DESCRIPTION OF THE INVENTION

It has been discovered that useful ether alkoxylates may be made by the amination of aryl polyethoxylates or alkyl polyethoxylates and then subsequent additional alkoxylation. The etheramine alkoxylates have potential uses as wetting agents, surfactants, emulsifiers, and detergents. The lower steric bulk of these products should allow more facile reaction with $CH_3Cl$ and other quaternizing agents to prepare the quaternary ammonium salts thereof which are expected to have surfactant properties.

Etheramines alkoxylates prepared in accordance with the method of the invention are expected to be less expensive than those made using tallowamine.

The etheramine alkoxylates of this invention have the formula:

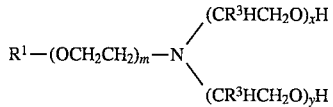

where $R^1$ is a straight or branched alkyl, aryl or alkylaryl group of 6 to 22 carbon atoms; $R^3$ are independently hydrogen or $C_1$–$C_3$ alkyl; m averages from about 1 to about 20; and x and y each independently average from about 0 to 30, where x+y averages from about 2 to about 60. The aryl groups in $R^1$, if present, may have from 5–7 carbon atoms and may or may not be substituted with moieties. In one embodiment of the invention, $R^3$ are independently hydrogen or methyl. When $R^3$ is hydrogen, the etheramine alkoxylates are etheramine ethoxylates. It is preferred, in one embodiment of the invention, that m averages from about 1 to about 10. and x+y averages from about 2 to about 5. In still another preferred embodiment of the invention, $R^1$ is a straight or branched alkyl group averaging from about 12 to 14 carbon atoms; $R^3$ are independently hydrogen or methyl; m averages from about 1 to about 3; and x+y averages from about 2 to about 5. An example of an especially preferred surfactant has: $R^1=C_{12}$–$C_{14}$ alkyl, $R^3$=hydrogen, m=3, and x+y=5.

The structure of formula I described above provides the well segregated hydrophobic tail and hydrophilic head necessary for a surfactant. In addition, the structure described in formula I above has the requisite HLB (Hydrophile/Lipophile Balance) to render it an emulsifier. The amount of ethylene oxide (x+y) can be tailored to produce a water soluable emulsifier or an oil soluable emulsifier.

The starting materials for the etheramine alkoxylates of this invention may be an ethoxylated alcohol or phenol of the formula:

$R^1$—$(OCH_2CH_2)_m$—OH where $R^1$ is a straight or branched alkyl, aryl or alkylaryl group of 6 to 22 carbon atoms; and m averages from about 1 to about 20 with the same provisos as above. These materials themselves may be prepared by the ethoxylation of alcohols and phenols having straight or branched alkyl substituents of 6 to 22 carbon atoms in the presence of an ethylene oxide and a catalyst using conventional techniques. The catalyst may typically be an alkali metal hydroxide catalyst such as sodium hydroxide or potassium hydroxide or sodium methylate or the like.

The ethoxylated alcohol or phenol is aminated in the presence of ammonia and an amination catalyst to produce an etheramine. The amination step of this invention is conducted at a temperature in the range from about 100° to about 300° C., preferably from about 190° to about 220° C., and at a pressure in the range of from about 500 to about 5000 psi.

The etheramine is next alkoxylated with an alkylene oxide using conventional techniques to produce etheramine alkoxylates. For example, the alkylene oxide may be selected from the group consisting of ethylene oxide, propylene oxide, n-butylene oxide, t-butylene oxide, and the like and mixtures thereof, as described previously. Again, preferred alkylene oxides are ethylene oxide, propylene oxide and mixtures thereof, with ethylene oxide by itself being especially preferred.

The etheramine alkoxylates may be further quaternized using conventional quaternizing agents including, but not necessarily limited to methyl chloride, MeCl ($CH_3Cl$); methyl iodide, MeI ($CH_3I$); dimethyl sulfate (($CH_3)_2SO_4$); benzyl chloride ($C_6H_5CH_2Cl$); and the like.

The invention will now be further described with reference to the following non-limiting Examples which are provided for the purpose of illuminating the invention and not limiting it in any way.

A. Preparation of Etheramine Alkoxylates

EXAMPLES 1–5

Amination of Ethoxylated EPAL® 1214

The polyol used in this amination was a 3 mole ethylene oxide adduct of EPAL 1214 (a $C_{12}$–$C_{14}$ linear alcohol made by Ethyl Corporation), and had a hydroxyl number of 175 mg KOH/g (3.12 meq/g). The amination was performed in a 600 cc tubular reactor fully charged with 425 g of a ⅛ in. extruded 38.4 wt. % Ni, 5.9 wt. % Cu, 1.1 wt. % Cr, and 0.7 wt. % Mo catalyst, on a gamma alumina support.

The polyol, ammonia, and hydrogen were each continuously fed to the reactor at about 0.5 lb/hr, 0.75 lb/hr, and 21.2 l/hr (STP), respectively. Samples were taken at several reactor temperatures. These were stripped of light components and water and then analyzed. Tabulated data are shown below in Table I. Examples 1–4 correspond to small 100 g collections of products. Example 5 was collected over 53 hours, and corresponds to 26.03 lbs of polyol feed and 38.57 lbs of ammonia feed.

TABLE I

| | Examples 1–5 | | | | |
|---|---|---|---|---|---|
| Example | 1 | 2 | 3 | 4 | 5 |
| Hot Spot Temp., °C. | 190 | 200 | 210 | 220 | 196 |
| Polyol, lb/hr | 0.52 | 0.50 | 0.50 | 0.52 | 0.49 |
| Ammonia, lb/hr | 0.71 | 0.72 | 0.76 | 0.76 | 0.73 |

TABLE I-continued

| | Examples 1–5 | | | | |
|---|---|---|---|---|---|
| Example | 1 | 2 | 3 | 4 | 5 |
| Hydrogen, l/hr | 21.2 | 21.2 | 21.2 | 21.2 | 21.2 |
| Total Acetyl.[1], meq/g | 3.02 | 2.79 | 2.58 | 2.42 | 2.906 |
| Total Amine, meq/g | 2.30 | 2.64 | 2.46 | 2.36 | 2.656 |
| Primary Amine, meq/g | 21.9 | 2.30 | 1.89 | 1.66 | 2.389 |
| Sec. Amine, meq/g | 0.11 | 0.34 | 0.57 | 0.70 | 0.27 |
| Acet. + Sec. Amine (total functionality) | 3.13 | 3.13 | 3.15 | 3.12 | 3.17 |
| % Conversion[2] | 77.0 | 95.2 | 96.2 | 98.1 | 92.1 |
| % Selectivity[3] to Primary Amine | 90.9 | 77.2 | 62.4 | 54.2 | 81.7 |

[1]Total Acetyl. = Total Acetylatables
[2]% Conv. is calculated by (Primary Amine + 2 × Secondary Amine)/(Acet. + Sec. Amine) × 100
[3]% Selec. is determined by (Primary Amine)/(Primary Amine + 2 × Secondary Amine) × 100

The etheramine of Example 5 described above was subsequently ethoxylated with 5, 10 and 15 moles EO, respectively. The three products are characterized in Table II.

TABLE II

| | Etheramine Ethoxylates | | | |
|---|---|---|---|---|
| Ex. No. | OH# (mg/g) | Total Amine (meq/g) | Tertiary Amine (meq/g) | pH |
| 6 | 184 | 1.685 | 1.670 | 9.81 |
| 7 | 133 | 1.20 | 1.18 | 9.91 |
| 8 | 111 | 0.974 | 0.965 | 10.04 |

An alternative approach to making etheramines ethoxylates involves reacting a long chain alkyl alcohol, such as cocoamine, with acrylonitrile to form an etheramine. The etheramine can then be alkoxylated and quaternized. A possible sequence is shown below:

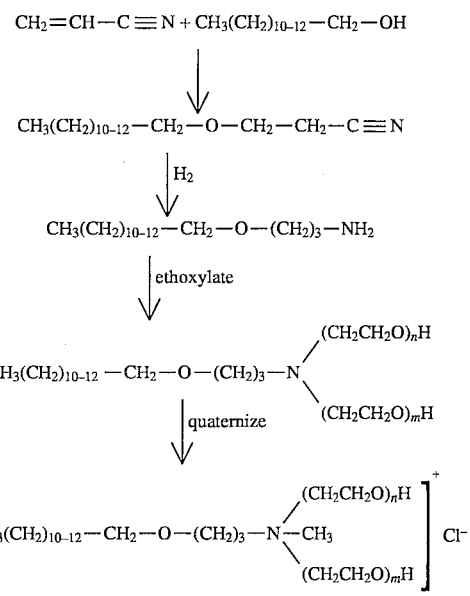

Again, it is expected that the surfactant properties of a compound made in this way would be very similar to the quaternary amine salt of ethoxylated tallowamine.

EXAMPLE 9

Alternate Route of Preparing Etheramine Ethoxylates

1. Preparation of Ethernitrile

In the first preparation of ethernitrile, the yield was 94% ethernitrile as analyzed by NMR. In a subsequent experiment, the yield to ethernitrile was 99% by NMR. In this latter experiment, 5027 g of EPAL 1214 and 460.3 g of potassium fluoride on alumina catalyst were charged to a three gallon autoclave. The temperature was raised to 50° C. Then 1629 g of acrylonitrile was added while the temperature was kept below 60° C. After the addition was complete, the reaction was allowed to proceed at 60° C. for four hours.

The catalyst was filtered off from the product under a nitrogen blanket. The pH of a 1% solution of the product was measured to be 7.17. The product was stirred with 200 g of Amberlyst® 15 resin at room temperature. After the resin was filtered off from the product, the pH of a 1% solution was measured to be 5.85.

2. Hydrogenation of Ethernitrile

Hydrogenation of the second ethernitrile prepared above gave an etheramine which was analyzed to be 97% etheramine and 3% alcohol, by NMR. The preparation involved charging 500 g of the aforementioned ethernitrile and 48 g of a cobalt-copper-chromium catalyst to a 1 liter autoclave. The autoclave was closed and flushed twice with hydrogen. Then, 60 g of ammonia was added and hydrogen was pressured in to 1000 psig. The temperature was raised to 150° C. Hydrogen was added to maintain a pressure of 3000 psig at 150° C. until no pressure drop was noted.

3. Ethoxylation of Etheramine

The aforementioned etheramine was ethoxylated using conventional techniques as mentioned earlier, with 5, 10 and 15 moles of EO, respectively. These products are characterized in Table III below:

TABLE III

| | | Etheramine Ethoxylates | | |
|---|---|---|---|---|
| Example | Moles EO | Total Acetylatables (meq/g) | Total Amine (meq/g) | Tertiary amine (meq/g) |
| 9A | 5 | 259 | 2.17 | 2.16 |
| 9B | 10 | 181 | 1.39 | 1.39 |
| 9C | 15 | 143 | 1.08 | 1.07 |

Many modifications may be made in the process of this invention without departing from the spirit and scope thereof which are defined only in the appended claims. For example, one skilled in the art may discover that a certain combination or proportion of alkylene oxides in the initial alkoxylated alcohol or phenol or added to the etheramine may give advantageous properties, or that certain quaternizing compounds reacted with the etheramine alkoxylates may give materials with improved characteristics. Further, the etheramine alkoxylates and quats thereof may find application in such formulations as spreading agents, cosmetics, personal care and household cleaning formulations.

We claim:

1. Etheramine alkoxylates of the formula:

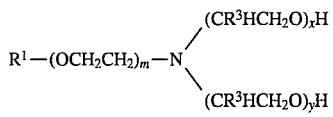

where $R^1$ is a straight or branched alkyl, aryl or alkylaryl group of 6 to 22 carbon atoms;
$R^3$ are independently hydrogen or $C_1$–$C_3$ alkyl;
m averages from about 3 to about 20; and
x and y each independently average from about 0 to 30, where x+y averages from about 5 to about 60 and where x and y are not both 0.

2. The etheramine alkoxylates of claim 1 where $R^3$ is hydrogen and the etheramine alkoxylates are etheramine ethoxylates.

3. The etheramine alkoxylates of claim 1 where m averages from about 3 to about 10, and x+y averages about 5.

4. The etheramine alkoxylates of claim 1 where $R^1$ is a straight or branched alkyl group averaging from about 12 to 14 carbon atoms; $R^3$ are independently hydrogen or methyl; m averages about 3; and x+y averages about 5.

5. A process for making the etheramine alkoxylates of claim 1 comprising aminating an alkoxylated alcohol or phenol of the formula

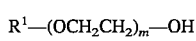

where $R^1$ is a straight or branched alkyl, aryl or alkylaryl group of 6 to 22 carbon atoms; and m averages from about 1 to about 20; in the presence of ammonia and an amination catalyst comprising nickel, copper, chromium and molybdenum; to produce an etheramine; and alkoxylating the etheramine with an alkylene oxide selected from the group consisting of ethylene oxide and propylene oxide to produce etheramine alkoxylates.

6. The process of claim 5 where the aminating is conducted at a temperature in the range from about 100° to about 300° C. and a pressure in the range of from about 500 to about 5000 psi.

7. Etheramine alkoxylates of the formula:

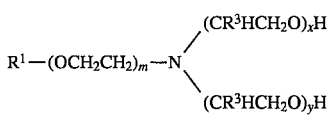

where $R^1$ is a straight or branched alkyl, aryl or alkylaryl group of 6 to 22 carbon atoms;
$R^3$ are independently hydrogen or $C_1$–$C_3$ alkyl;
m averages from about 3 to about 20; and
x and y each independently average from about 0 to 30, where x+y averages from about 5 to about 60 and where x and y are not both 0, which are made by the process comprising aminating an alkoxylated alcohol or phenol of the formula

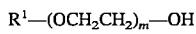

where $R^1$ and m are defined as above; in the presence of ammonia and an amination catalyst comprising nickel, copper, chromium and molybdenum; to produce an etheramine; and alkoxylating the etheramine with an alkylene oxide selected from the group consisting of ethylene oxide and propylene oxide to produce the etheramine alkoxylates.

8. The etheramine alkoxylates of claim 7 where in the process, the aminating is conducted at a temperature in the range from about 100° to about 300° C. and a pressure in the range of from about 500 to about 5000 psi.

* * * * *